US006426090B1

(12) United States Patent
Ream et al.

(10) Patent No.: US 6,426,090 B1
(45) Date of Patent: Jul. 30, 2002

(54) OVER-COATED PRODUCT INCLUDING TABLETED CENTER AND MEDICAMENT

(75) Inventors: Ronald L. Ream, Plano; Leonard Matulewicz, Oswego; William J. Wokas, Bolingbrook, all of IL (US)

(73) Assignee: Wm. Wrigley Jr. Company, Chicago, IL (US)

( * ) Notice: Subject to any disclaimer, the term of this patent is extended or adjusted under 35 U.S.C. 154(b) by 0 days.

(21) Appl. No.: 09/955,870

(22) Filed: Sep. 19, 2001

Related U.S. Application Data

(60) Division of application No. 09/631,326, filed on Aug. 3, 2000, which is a continuation-in-part of application No. 09/618,808, filed on Jul. 18, 2000, which is a continuation-in-part of application No. 09/510,878, filed on Feb. 23, 2000, which is a continuation-in-part of application No. PCT/US99/29742, filed on Dec. 14, 1999, which is a continuation-in-part of application No. 09/286,818, filed on Apr. 6, 1999.

(51) Int. Cl.$^7$ .............................. A61K 9/20; A61K 9/68
(52) U.S. Cl. ...................... 424/464; 424/48; 424/465; 424/440
(58) Field of Search ................. 424/440, 464, 424/465, 48; 426/5

(56) References Cited

U.S. PATENT DOCUMENTS

| | | | |
|---|---|---|---|
| 4,250,195 A | | 2/1981 | Cherukuri et al. |
| 4,317,838 A | * | 3/1982 | Cherukuri et al. ............. 426/5 |
| 4,386,106 A | | 5/1983 | Merrit et al. |
| 4,753,805 A | * | 6/1988 | Cherukuri et al. ............. 426/5 |
| 5,139,794 A | | 8/1992 | Patel et al. |
| 5,536,511 A | | 7/1996 | Yatka |
| 5,665,406 A | | 9/1997 | Reed et al. |
| 6,200,604 B1 | | 3/2001 | Pather et al. |
| 6,258,376 B1 | | 7/2001 | Athanikaar |

FOREIGN PATENT DOCUMENTS

WO          WO 99/27798          6/1999

OTHER PUBLICATIONS

Beckett, A.H., et al.; "Buccal absorption of basic drugs and its application as an in vivo model of passive drug transfer through lipid membranes" (1967) *J. Pharm. Pharmac.*, 19 Suppl. 31S–41S.

Weinberg, David. S., et al.; "Sublingal absorption of selected opioid analgesics" (1988) *Clin. Pharmacol Ther.*, 44: 335–342.

* cited by examiner

*Primary Examiner*—Thurman K. Page
*Assistant Examiner*—S. Howard
(74) *Attorney, Agent, or Firm*—Bell, Boyd & Lloyd LLC

(57) ABSTRACT

Methods and products for delivering a medicament or agent to an individual are provided as well as methods for producing the product. The product includes a coating having a medicament or agent. The medicament or agent is present within the coating that surrounds a tableted center. The tableted center is defined by compressible excipients. By chewing the product, the medicament or agent is released from the product within the buccal cavity.

15 Claims, 1 Drawing Sheet

OVER-COATED PRODUCT INCLUDING TABLETED CENTER AND MEDICAMENT

This is a divisional of U.S. patent application Ser. No. 09/631,326 filed on Aug. 3, 2000, which is a continuation-in-part of U.S. patent application Ser. No. 09/618,808, filed on Jul. 18, 2000, which is a continuation-in-part of U.S. patent application Ser. No. 09/510,878, filed on Feb. 23, 2000, which is a continuation-in-part of U.S. patent application Ser. No. 09/286,818, filed on Apr. 6, 1999 and PCT Patent Application No. PCT/US99/29742 filed on Dec. 14, 1999.

BACKGROUND OF THE INVENTION

The present invention generally relates to the delivery of medicaments and other agents. More specifically, the present invention relates to the delivery of medicaments and agents using chewing gum formulations and methods for producing such products.

It is of course known to provide agents to individuals for various purposes. These agents can be used to treat diseases and as such are typically referred to as drugs or medicaments. Likewise, the drugs or medicaments can be used for prophylactic purposes. Still, it is known to provide agents to an individual for a variety of non-medical purposes including enhancing performance or maintaining or initiating alertness. There are a great variety of such agents. These agents run the gamut from stimulants such as caffeine to drugs such as analgesics, tranquilizers, cardiovascular products, insulin, etc. Some such agents are taken on an as needed basis while other agents must be taken at regular intervals by the individual.

Typically, drugs (medicaments) are administered parenterally or enterally. Of course, parenteral administration is the administration of the drug intravenously directly into the blood stream. Enteral refers to the administration of the drug into the gastrointestinal tract. In either case, the goal of the drug administration is to move the drug from the site of administration towards the systemic circulation.

Except when given intravenously, a drug must traverse several semipermeable cell membranes before reaching general circulation. These membranes act as a biological barrier that inhibits the passage of drug molecules. There are believed to be four processes by which drugs move across a biological barrier: passive diffusion; facilitated diffusion; active transport; and pinocytosis.

Passive diffusion is the transport across the cell membrane wherein the driving force for the movement is the concentration gradient of the solute. In orally administered drugs, this absorption occurs in the small intestines. Facilitated diffusion is believed to be based on a carrier component that combines reversibly with the substrate molecule at the cell membrane exterior. The carrier substrate complex diffuses rapidly across the membrane with release of the substrate at the interior surface. Active transport requires an energy expenditure by the cell and appears to be limited to agents with structural similarities to normal body constituents. These agents are usually absorbed from specific sites in the small intestines. Pinocytosis refers to the engulfing of particulars or fluid by a cell. It is believed to play a minor role in drug transport. *Merck Manual*, 16th Edition, pp. 2598–2599.

In determining the efficacy of a drug and the effectiveness of the use of a drug to treat a disease, drug absorption is a critical concern. Drug absorption refers to the process of drug movement from the site of administration toward the systemic circulation.

Oral administration of drugs is by far the most common method. When administered orally, drug absorption usually occurs due to the transport of cells across the membranes of the epithelial cells within the gastrointestinal tract. Absorption after oral administration is confounded by numerous factors. These factors include differences down the alimentary canal in: the luminal pH; surface area per luminal volume; perfusion of tissue, bile, and mucus flow; and the epithelial membranes. See *Merck Manual* at page 2599.

A further issue effecting the absorption of orally administered drugs is the form of the drug. Most orally administered drugs are in the form of tablets or capsules. This is primarily for convenience, economy, stability, and patient acceptance. Accordingly, these capsules or tablets must be disintegrated or dissolved before absorption can occur. There are a variety of factors capable of varying or retarding disintegration of solid dosage forms. Further, there are a variety of factors that effect the dissolution rate and therefore determine the availability of the drug for absorption. See *Merck Manual* at page 2600.

Parenteral administration allows for the direct placement of the drug into the blood stream. This usually insures complete delivery of the dose to the general circulation. However, administration by a route that requires drug transfer through one or more biologic membranes to reach the blood stream precludes a guarantee that all of the drug will eventually be absorbed. Even with parenteral administration, because capillaries tend to be highly porous, the perfusion (blood flow/gram of tissue) is a major factor in the rate of absorption. Thus, the injection site can markedly influence a drugs' absorption rate; e.g., the absorption rate of diazepam injected IM into a site with poor blood flow can be much slower than following an oral dose. See *Merck Manual* at page 2601.

Not only is drug absorption an issue in drug delivery but also the bioavailability of the drug is also critical. Bioavailability is defined as the rate at which and the extent to which the active moiety (drug or metabolite) enters the general circulation, thereby gaining access to the site of action. Bioavailability depends upon a number of factors, including how a drug product is designed and manufactured, its physicochemical properties, and factors that relate to the physiology and pathology of the patient. See *Merck Manual* at page 2602.

When a drug rapidly dissolves from a drug product and readily passes across membranes, absorption from most site administration tends to be complete. This is not always the case for drugs given orally. Before reaching the vena cava, the drug must move down the alimentary canal and pass through the gut wall and liver, which are common sites of drug metabolism. Thus, the drug may be metabolized before it can be measured in the general circulation. This cause of a decrease in drug input is called the first pass effect. A large number of drugs show low bioavailability owing to an extensive first pass metabolism. The two other most frequent causes of low bioavailability are insufficient time in the GI tract and the presence of competing reactions. See *Merck Manual* at page 2602.

Bioavailability considerations are most often encountered for orally administered drugs. Differences in bioavailability can have profound clinical significance.

Although parenteral administration does provide a method for eliminating a number of the variables that are present with oral administration, parenteral administration is not a preferable route. Typically, parenteral administration requires the use of medical personnel and is just not warranted nor practical for the administration of most agents and drugs, e.g., analgesics. Even when required, parenteral administration is not preferred due to patient concerns including comfort, infection, etc., as well as the equipment and costs involved. However, despite best efforts certain therapies require parenterally injected drugs. For example, research for decades has focused on an attempt to deliver insulin to an individual through a non-parenteral means. Despite such efforts, today insulin is still only administered intravenously.

In producing products for delivering medicaments and other agents to an individual, it may be critical that a predefined amount of medicament or agent is delivered per dose of the product. This allows the physician and/or patient to determine the amount of product to ingest and insure that a safe and effective level of medicament or agent is delivered. If the medicament or agent is located in a coating of the product it is necessary to ensure that definite levels of coating are present in each product. This requires a manufacturing process that allows for the accurate production of coated products.

A still further issue vis-a-vis drug delivery, and most specifically oral drug delivery, is taste. Many over the counter and pharmaceutical products are not available in a chewable form due to taste problems. Such products include, for example, excedrin, pseudoephedrin, and Ma Huang/guarana diet pills.

Thus, there is a need for an improved method of delivering drugs and agents to an individual.

SUMMARY OF THE INVENTION

The present invention provides improved methods for manufacturing products for delivering a medicament or agent to an individual as well as such products. To this end, a compressible excipient is tableted and then coated to produce a coated product including a medicament or agent. The medicament or agent is present within the coating or shell that substantially encloses the tableted compressible excipient. It has been found that by tableting the compressible excipient that a specifically defined coating can be provided, providing a predetermined and controllable level of medicament or agent.

The excipient can be, by way of example and not limitation, dextrose, sucrose, or other saccharides, sorbitol, mannitol, iso-malitol, other compressible sugar alcohols, or combinations thereof.

Improved formulations including medicaments or agents are also provided by the present invention.

To this end, the present invention provides a product including a tableted compressible excipient. The tableted compressible excipient is substantially surrounded by a coating. The coating includes a medicament or agent and comprises at least 50% by weight of the product.

In an embodiment, the coating includes a masking agent to assist in improving the organoleptic properties of the coating containing the medicament. The masking agent may be chosen from the group consisting of: sucralose; zinc gluconate; ethyl maltol; glycine; acesulfame-K; aspartame; saccharin; fructose; xylitol; spray dried licorice root; glycerrhizine; dextrose; sodium gluconate; glucono delta-lactone; ethyl vanillin; vanillin; normal and high-potency sweeteners; and a variety of appropriate flavors.

In an embodiment, the coating includes a high-intensity sweetener. In a further embodiment, the high-intensity sweetener is chosen from the group consisting of aspartame, sucralose, and acesulfame-K.

In an embodiment, the compressible excipient is chosen from the group consisting of dextrose, sucrose, sorbitol, manitol, and combinations of same.

In an embodiment, the coating comprises 50% to 75% by weight of the product.

In an embodiment, the coating is a recrystallized granular coating.

In an embodiment, the coating is an amorphous coating.

In an embodiment, the coating is a powder coating.

In an embodiment, the medicament is chosen from the group consisting of: analgesics; muscle relaxants; antacids; antihistamines; decongestants; anti-inflammatories; antibiotics; antivirals; psychotherapeutic agents; insulin; nutraceuticals; nutritional supplements; and cardiovascular agents.

In another embodiment of the present invention a method of drug delivery is provided. The method comprising the steps of: providing a product that includes a compressible excipient that is substantially surrounded by a coating, the coating includes a medicament; chewing the product to cause the medicament to be released from the product into the buccal cavity of the chewer; and continuing to chew the product thereby creating a fluid pressure causing the medicament to enter the systemic system of the chewer through the oral mucosa contained in the buccal cavity.

In an embodiment of the method, the agent is a medicament. In an embodiment of the method, the medicament is chosen from the group consisting of: analgesics; muscle relaxants; antihistamines; decongestants; antacids; anti-inflammatories; antibiotics; antivirals; psychotherapeutic agents; insulin; nutraceuticals; nutritional supplements; and cardiovascular agents.

In yet another embodiment of the present invention a method of delivering a medicament is provided. The method comprising the steps of: providing a product including a coating that comprises at least 50% by weight of the product and surrounds a tableted compressible excipient. The coating includes a medicament; and chewing the product.

In a still further embodiment of the present invention a product containing a medicament or agent is provided. The product includes a tableted compressible excipient center. The coating surrounds the tableted center and includes a medicament. The coating comprising at least 50% by weight of the product. The coating includes taste masking agents.

Moreover, in an embodiment of the present invention, a method of manufacturing a product containing a medicament or agent is provided. The method comprising the steps of: preparing a tableted compressible excipient center; and coating the tableted center with a powder and a syrup to create a coated product, at least one of the powder or syrup portion including a medicament or agent.

In an embodiment the powder and syrup are coated on the compressible excipient in alternating steps until a sufficient coating has been built up.

In an embodiment the coating has a polished finish.

Accordingly, an advantage of the present invention is to provide new methods for manufacturing products for delivering medicaments or agents to an individual.

Furthermore, an advantage of the present invention is to provide an improved product containing a medicament.

Additionally, an advantage of the present invention is to provide a method for administering medicaments that is more palatable than current methods.

Still further, an advantage of the present invention is to provide a method of delivering medicaments to an individual that provides for increase absorption and bioavailability as compared to medicaments that are designed to be absorbed in the GI tract.

Further, an advantage of the present invention is to provide a method of administering a medicament or agent to an individual at a lower level than is typically administered orally while still achieving the same effect.

Furthermore, an advantage of the present invention is to provide a method for administering medicaments or agents to an individual that heretofore were administered parenterally.

Another advantage of the present invention is to provide a method for manufacturing products including medicaments or agents in the coating.

Moreover, an advantage of the present invention is to provide an improved method for drug delivery.

Further, an advantage of the present invention is to provide a chewable product that contains an agent that heretofore could not be provided in a chewable form that was palatable.

Still, an advantage of the present invention is to provide a method for ensuring that a coated product that includes a medicament has a precise level of medicament.

An advantage of the present invention is that a coated product is provided wherein the coating can absorb or lose moisture without apparent degradation.

Further, an advantage of the present invention is that a coated chewing gum product including medicament is provided having an extended shelf-life.

Furthermore, an advantage of the present invention is that it can produce medicament-containing products having precise sizes and shapes.

Another advantage of the present invention is to provide a method of controlling the amount of agent containing coating that is used on a coated product.

Additional features and advantages of the present invention will be described in and apparent from the detailed description of the presently preferred embodiments and the figures.

DETAILED DESCRIPTION OF THE PRESENTLY PREFERRED EMBODIMENTS

Figure 1:
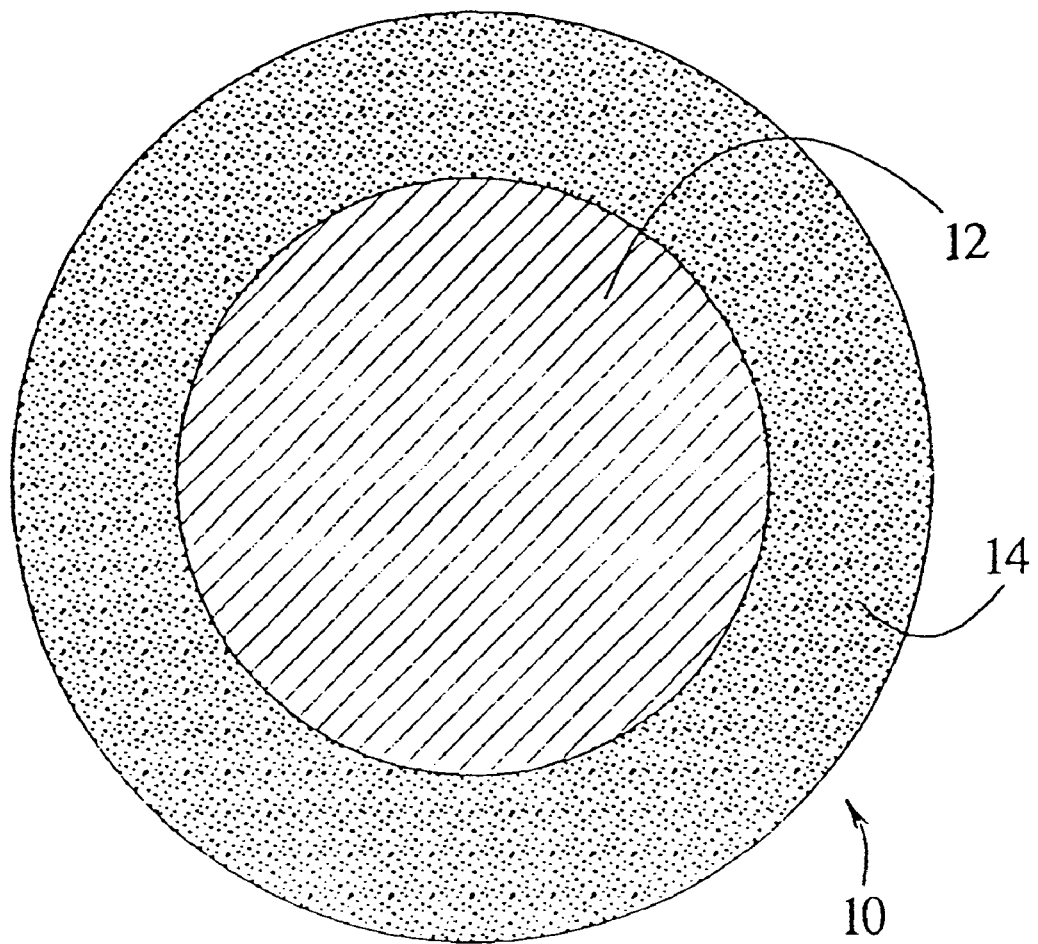
FIG. 1 illustrates generally an embodiment of the product of the present invention.

The present invention provides improved methods for delivering medicaments and other agents to an individual as well as improved products including such medicaments or agents and methods for producing same.

Pursuant to the present invention, a medicament or agent is contained in a coating that surrounds a tableted compressible excipient center. As used herein "tableted" means that a center is provided that has a precise size (within an acceptable range) depending on the medicament or agent and shape. Thus allows an accurate control of the coating as well as allows one to create products having specific sizes and shapes. In a preferred embodiment, the coating comprises at least 50% by weight of the entire product.

As the product is chewed, the medicament or agent is released into the saliva. During continual chewing or crunching of the product between the teeth, the medicament or agent in the saliva is then forced through the oral mucosa in the buccal cavity due to the pressure created by the chewing. The oral mucosa has a thin epithelium and a rich vascularity. Thus, the oral mucosa favors drug absorption. In contrast to a typically orally ingested drug, wherein the solution is in contact too briefly for absorption to be appreciable through the oral mucosa, it is believed that during chewing, the agent and/or medicament remains in the buccal cavity and is forced through the oral mucosa. Also it has been surprisingly found that an increase in the absorption of the drug is achieved as well as an increase in the bioavailability of the drug as compared to typical oral administration. It has been found that the drug or agent is absorbed much quicker than if it was swallowed as in a typical oral administration. Indeed, the absorption approaches that of a parenteral administration, and bioavailability is also much greater than oral administration.

Referring to FIG. 1, an embodiment of the product 10 of the present invention is illustrated. As illustrated, the product 10 includes a tableted center 12. The tableted center can be any compressible excipient known in the art. Examples of such excipients include saccharides such as dextrose and sucrose, and sugar alcohols such as sorbitol and mannitol, and combinations of same.

Pursuant to the present invention, surrounding the tableted center 12 is a coating 14. The coating 14 includes a medicament or other active agent.

As noted above, the tableted center 12 can be any size or shape, although in a referred embodiment the center has a round shape. However, the key is that by tableting the center, one can control to a precise relative standard deviation, the size of the center 12. This allows one to accurately control the amount of coating 14 that is placed around the center 12 to create the resultant product. In this regard, if the center is too large or too small, the resultant coating will either be greater or less than desired. Because the coating, as noted below, contains a medicament, if the size of the center 12 is not the predetermined size, the level of medicament present in the resultant product could vary. By precisely controlling the size of the center, through the tableting process, one is ensured that a precise level of coating, and therefore medicament, can be provided and thereby delivered.

Additionally, by using the tableting process one can vary the size and shape of the resultant product. For example, for a product including an analgesic, the product can have an aspirin shape. In a similar vein, for proprietary designs that are used for certain drugs, one can create the tableted center in the proprietary design allowing the resultant product to have the proprietary shape or design.

A variety of different tableting processes can be used. What is important is that a process is used that allows one to create a uniform center. For example, conventional drug tableting equipment or confectionary tableting product equipment can be utilized. An example of such equipment is the Stokes tableting machine available from Stokes Manufacturing Inc.

Referring now to the coating 14, preferably, the coating 14 comprises approximately 50% to about 75% by weight of the product. A variety of coatings can be utilized. For example, the coating can be a soft amorphous coating. Or, the coating can be a recrystallized granular coating. As discussed below, in a preferred embodiment, the coating is applied as a syrup/powder composition.

Preferably, the coating 14 will include masking agents. In this regard, high-intensity sweeteners and appropriate flavors can be used to help mask, along with the tableted center, any off notes that are present due to the medicament or agent. It has been found that with respect to certain medicaments or agents that may have an astringent or bitter taste that by adding a masking agent to the formulation, that a much more palatable formulation, including the medicament, can be provided. In this regard, even though the medicament in for example, its powder form may be bitter or have an offensive taste, the matrix used as the coating of the present invention, including the masking agent, will help, along with the tableted center, to afford a product having acceptable organoleptic properties. For example, it has been surprisingly found that by solubilizing a powdered matrix of medicament and masking agent, this increases the ability of the masking agent to cover up bitter and bad flavors produced by the medicament or agent. By selecting specific masking agents in combination with the compressible excipients, based on the bad or off taste produced by the medicament, one can provide a palatable formulation.

For example, if one is attempting to cover an astringent flavor such as aspirin, one could use masking agents found to be effective against astringency such as fructose and high-intensity sweeteners, e.g. saccharin, aspartame, sucralose, and acesulfame-k. In the case of a moderately bitter active ingredient, such as caffeine, one would use ingredients such as glycine, ethyl maltol, zinc gluconate, licorice root powder, high-intensity sweeteners, etc. In the case of a very bad tasking active ingredient such as acetaminophen it has been found that peppermint functions very well, but, may need to be augmented with a high-intensity sweetener, such as, for example, aspartame.

The masking agents, in an embodiment, are selected from the group consisting of: sucralose; zinc gluconate; ethyl maltol; glycine; acesulfame-k; aspartame; saccharin; fructose; xylitol; maltitol; isomalt; salt; spray dried licorice root; glycerrhizine; dextrose; sodium gluconate; sucrose; glucono delta-lactone; ethyl vanillin; and vanillin.

In an embodiment of the invention, sufficient masking agent and/or tableted excipient will be used to improve and provide acceptable organoleptic properties to the product. As used herein to provide "acceptable organoleptic properties" means that the product will have a sufficiently pleasant, or at least non-offensive taste, to allow the consumer to chew the product allowing at least a portion of the product to dissolve in the mouth of the consumer. Whether a masking agent is necessary and/or the amount of masking agent will vary depending on medicament or agent and compressible excipient. Of course, if desired, more than one masking agent can be used, e.g., zinc gluconate and a sweetener or flavor. In an embodiment, the masking agent may comprise approximately 30% to about 99% by weight of the coating formulation.

In a preferred embodiment, the coating includes a high-intensity sweetener such as aspartame, sucralose, and acesulfame-k. Preferably, the high-intensity sweetener comprises approximately 0.1% to about 5% by weight of the coating. As noted above, the coating will include a medicament or agent. It is envisioned, that a variety of different medicaments and agents can be placed in the coating. For example, such agents include, inter alia, stimulants such as caffeine and nicotine. Generally, such medicaments include, inter alia, analgesics, antibiotics, antivirals, antihistamines, anti-inflammatories, decongestants, antacids, muscle relaxants, psychotherapeutic agents, insulin, diuretics, vitamins, minerals, anesthetics, antitussives, anti-diabetic agents, bioengineered pharmaceuticals, nutraceuticals, nutritional supplements, and cardiovascular agents. It is envisioned, that depending on the medicament, the resultant product can be used to treat, inter alia: coughs; colds; motion sickness; allergies; fevers; pain; inflammation; sore throats; cold sores; sinus problems; diarrhea; diabetics; gastritis; depression; anxiety; hypertension; angina; and other maladies and symptoms. Specific agents/medicaments include, by way of example and not limitation: caffeine; aspirin; acetaminophen; ibuprofen; ketoprofen; cimetodine; ranitidine; famotidine; dramamine; omeprazole; dyclonine; chlorpheniramine maleate; pseudoephedrine; hydrochloride; dextromethorphan hydrobromide; benzocanine; sodium naproxen; nicotine; hydroxycitric acid; chromium picolinate; phosphatidylserine; nicotine; insulin; echinacea purpurea; zinc; vitamin C; ginseng; kola nut; capsicum; nettle; passion flower; St. Johns Wort; valerian; Ma Huang/guarana; kava kava; and chamomile.

It is believed that the product of the present invention will allow chewable products to be provided that heretofore were not provided due to offensive taste. Such products include, by way of example and not limitation, excedrin, pseudoephedrin, and Ma Huang/guarana diet pills.

Preferably, the agents or medicaments are contained in the coating of the product at levels of approximately 50 micrograms to 500 milligrams. The specific levels will depend on the active ingredient. For example, if chromium picolinate is the active ingredient in an embodiment, it would be present at a level of 50 micrograms per serving (3.0 grams of coated product); aspirin would be preset at a level of 325 milligrams per 3.0/gram serving. The level of medicament or agent in the coating of the product is selected so as to create, when the product is chewed, a sufficiently high concentration of the medicament or agent in the saliva.

For example, when the agent is a stimulant such as nicotine or caffeine, the level of the stimulant in the coating of the product should be such that it creates a saliva content of stimulant of approximately 15 to 440 ppm after the product is chewed. At this level, a sufficient amount of stimulant will be delivered to the chewer to create the effects set forth in the application. For a botanicals (e.g., chamomile, kava, kola, nut, ginseng, and Echinacea), the agent should be present in a sufficient amount to create a saliva content of approximately 85 to 1100 ppm after the product is chewed. For a metabolizer, for example, chromium picolineate and hydroxi-chitic acid, the agents should be present in an amount to create a saliva content of approximately 0.5 to about 900 ppm after the product is chewed. If the agent is a vitamin or mineral (e.g., phosphatidy serine, vitamin C, and zinc), the agent should be present in the amount to create a saliva content of the vitamin or mineral of approximately 10 to about 250 ppm after the product is chewed.

The level of medicament or agent in the coating is selected so as to create, when the product is chewed, a sufficiently high concentration of the medicament or agent in the saliva.

For example, when the agent is a stimulant such as caffeine, the level of the stimulant in the compacted powder formulation should be such that it creates a saliva content of stimulant of approximately 1% to about 66% after the formulation is placed in the mouth. At this level, a sufficient amount of stimulant will be delivered to the user to create the effects set forth in the application. If a medicament is used such as a medicinal (e.g., analgesics), sufficient medicinal should be present in the compacted powder formulation to create a salvia content of approximately 1% to about 66%. For botanicals (e.g., chamomile, kava, kola, nut, ginseng, and Echinacea), the agent should be present in a sufficient amount to create a saliva content of approximately 1% to about 66%. For a metabolizer, for example, chromium picolineate and hydroxi-chitic acid, the agents should be present in an amount to create a saliva content of approximately 1% to about 66%. If the agent is a vitamin or mineral (e.g., phosphatidy serine, vitamin C, and zinc), the agent should be present in the amount to create a saliva content of the vitamin or mineral of approximately 2% to about 30%.

Pursuant to the present invention, depending on the agent or medicament, the dosing regiment will change. For example, if the medicament is an analgesic, the product would be taken on an as needed basis. Of course, similar to the oral administration of an analgesic, there would be restrictions on the doses taken, for example, not more often than one product every four hours and not more often than four to five times a day.

If the agent is a stimulant, such as caffeine, to be used to enhance performance than the product would be ingested, in a preferred embodiment ten minutes or less before the performance.

A variety of methods can be used for constructing the coating of the product. Typically coatings are applied to products in a three-phase operation. In this regard, the first phase is to add a crude coating of an alternate application of syrup and powder is applied. This is followed by a second phase called the finishing coating in which finer powder and longer tumbling is used to produce a smooth finish. Finally a shellacking and polishing third phase is performed to provide a high-sheen smooth finish. In a preferred embodiment, the second phase is not used and the third phase is optional. As noted above, in an embodiment, the products of the present invention can include 50% to 75% by weight coating. Using only the first phase of the method, this large percent of coating can be applied to the product in a realistic time-frame.

In an embodiment, the coating comprises approximately 10 to about 30% by weight syrup and approximately 70% to about 90% by weight powder. For example, in a preferred embodiment, the coating comprises 20% syrup and 80% powder.

In an embodiment of constructing the coated product, first the syrup is distributed on the center. Then a portion of the powder is sprinkled on top to dry up the syrup. A further amount of syrup is added and powder supplied. This process is continued until the necessary amount of syrup and powder have been applied to the exterior of the center, e.g., 10 to 20 coating layers or more are applied. The coating which can play an important role as the masking agent, can include a combination of sugar, corn syrups, or in the case of a sugar-free product, various combinations of sugar alcohols, monomers, and polymers.

It has been found that by using this type of gross up coating process that advantages are achieved for the product containing medicament of the present invention. This is true whether or not the medicament is contained in the powder or in the syrup. Accordingly, if desired, the medicament can be contained in the syrup rather than in the powder.

Pursuant to the present invention, the coated product may not include a shellac or other finishing or shiny layer. It has been found, that the coating can comprise merely a matte finish and still function, not only satisfactorily, but has some advantages. In this regard, typically coated products that retain moisture on the coating along with a shellac layer may degrade due to moisture in the coating and therefore do not have an extended shelf-life. This is especially true with the thick coatings of the present invention. Such thick coatings absorb more moisture than thinner coatings. If a matte finish is utilized, although the thick coating layer can absorb the moisture, the matte finish allows the moisture to move into and out of the coating layer. This thereby prevents degradation of the product. Thus, the present invention provides a product having a thick coating with increased shelf-life.

The matte finish additionally not only allows a thick coating to be used but also ingredients that have high moisture absorption. Due to the matte finish, high moisture absorbing medicaments can be used without undue product degradation.

In an embodiment of the coating, dextrose or sucrose or combinations thereof function as the main ingredient. In a preferred embodiment, dextrose is utilized and the dextrose comprises approximately 50 to about 90% of the coating. The active ingredients or medicaments, in the coating may comprise as much as 30% of the coating down to very small amounts as long as the medication is efficacious. In a preferred embodiment, the flavors are powdered flavors and can range from 0.1% to approximately 5%. High-intensity sweeteners such as aspartame, sucralose, and acesulfame-k can also be used in the coating and range from approximately 0.1 to about 5% of the coating. As noted above, these high-intensity sweeteners are excellent masking agents.

The coating including medicament or agent can surround a variety of different center compositions. In this regard, the center can be any compressible excipient. For example, the center can be a compressible saccharide, e.g., dextrose, maltose, fructose, or sucrose, or a combination of same, or a compressible sugar alcohol, e.g., sorbitol, mannitol, and isomalitol or combinations of same.

If desired, additional excipients can be used with the above, such as high-intensity sweeteners and flavoring agents.

Preferred sweeteners include, but are not limited to, sucralose, aspartame, salts of acesulfame, altitame, saccharin and its salts, cyclamic acid and its salts, glycerrhizinate, dihydrochalcones, thaumatin, monellin, and the like, alone or in combination. In order to provide longer lasting sweetness and flavor perception, it may be desirable to encapsulate or otherwise control the release of at least a portion of the artificial sweetener. Such techniques as wet granulation, wax granulation, spray drying, spray chilling, fluid bed coating, coacervation, and fiber extension may be used to achieve the desired release characteristics.

Flavoring agents may include essential oils, synthetic flavors or mixtures thereof including, but not limited to, oils derived from plants and fruits such as citrus oils, fruit essences, peppermint oil, spearmint oil, other mint oils, clove oil, oil of wintergreen, anise and the like. Artificial flavoring agents and components may also be used. Natural and artificial flavoring agents may be combined in any sensorially acceptable fashion.

TABLETED COATED PRODUCT
The tableted gum will include a center and a coating. In an embodiment, the center will include the following ingredients in the following ranges:

| Ingredient | Percent |
|---|---|
| Peppermint Flavor | 0.44 |
| Menthol Flavor | 0.37 |
| Dextrose | 97.49 |
| Magnesium Stearate | 1.70 |
| | 100.00% |
| Dextrose | 98.92 |
| Sucrolose | 0.19 |
| Bubble Gum Flavor | 0.19 |
| Magnesium Stearate | 1.70 |
| | 100.00% |

| Ingredient | Grams | Percent |
|---|---|---|
| Menthol Flavor | 30.00 | 1.88 |
| Eucalyptus Flavor | 2.00 | 0.13 |
| Aspartame | 32.00 | 2.00 |
| Magnesium Stearate | 27.20 | 1.70 |
| Dextrose | 1,508.80 | 94.30 |
| | 1,600.00 | 100.00% |

An embodiment of the coating for the product is as follows:

| Ingredient | Grams |
|---|---|
| Acetaminophen | 0.3490 |
| Peppermint Flavor (dry) | 0.0072 |
| Menthol Flavor (dry) | 0.0062 |
| Dextrose | 1.4200 |
| Sucrolose | 0.0030 |
| Aspartame | 0.0062 |
| Glucose | 0.2080 |
| | 2.0000 g |

| Center (1 gram) Ingredient | Percent | Coating (1 gram) Ingredient | Grams |
|---|---|---|---|
| ACETAMINOPHEN COATED PRODUCT ||||
| Peppermint Flavor | 0.44 | Acetaminophen | 80.0 |
| Menthol Flavor | 0.37 | Encapsulated | |
| Dextrose | 97.49 | Aspartame | 20.0 |
| Magnesium Stearate | 1.70 | Aspartame | 50.0 |
| | 100.00% | Salt Flour | 2.5 |
| | | Dextrose | 643.5 |
| | | Flavor | 4.0 |
| | | | 800.0 |

| Center (1 gram) Ingredient | % | Coating (2 grams) Ingredient | Grams |
|---|---|---|---|
| ACETAMINOPHEN COATED PRODUCT ||||
| Peppermint Flavor | 0.44 | Acetaminophen | 335.0 |
| Menthol Flavor | 0.37 | Natural Peppermint | 7.0 |
| Dextrose | 97.49 | S.D. Menthol | 6.0 |
| Magnesium Stearate | 1.70 | Dextrose | 1,221.0 |
| | 100.00% | Aspartame | 32.0 |
| | | | 1,601.0 g |

| Center (1 gram) Ingredient | Grams | Coating (2 grams) Ingredient | Grams |
|---|---|---|---|
| PSEUDOEPHEDRIN COATED PRODUCT ||||
| Peppermint Flavor | 0.44 | Dextrose | 1,476.00 |
| Menthol Flavor | 0.37 | Eucalyptus* | 2.00 |
| Dextrose | 97.49 | Menthol* | 30.00 |
| Magnesium Stearate | 1.70 | Aspartame | 32.00 |
| | 100.00% | Pseudoephedrin | 60.00 |
| | | | 1,600.00 |

| Gum Center (1 gram) Ingredient | Grams | Coating (2 grams) Ingredient | Grams |
|---|---|---|---|
| PEPPERMINT CAFFEINE COATED PRODUCT ||||
| Peppermint Flavor | 0.44 | Caffeine | 100.0 |
| Menthol Flavor | 0.37 | Peppermint | 13.0 |
| Dextrose | 97.49 | Dextrose | 1,455.0 |
| Magnesium Stearate | 1.70 | Aspartame | 32.0 |
| | 100.00% | | 1,600.0 |

*sprayed dried

By way of example, and not limitation, examples demonstrating the benefits of placing a medicament in a coating surrounding a chewable confectionary, chewing gum, will now be provided.

Experiment No. 1

The following gum center formulation was made as a gum pellet center:

| Gum Center | % |
|---|---|
| Gum Base | 47.00 |
| Sorbitol | 39.52 |
| Liquid Sorbitol | 7.50 |
| Flavors | 2.36 |
| Encapsulated Flavors | 2.00 |

-continued

| Gum Center | % |
|---|---|
| Glycerin | 0.75 |
| Encapsulated Sweeteners | 0.87 |
| | 100.00 |

The gum pellet was coated with the following gum coating formulation:

| Gum Coating | % of Syrup 1 | % of Syrup 2 |
|---|---|---|
| Xylitol | 63.03 | 74.35 |
| Water | 11.14 | 13.15 |
| 40% Gum Tahla Solution | 20.87 | 7.96 |
| Titanium Dioxide Whitener | 0.37 | 0.44 |
| Peppermint Flavor[1] | 0.81 | 0.00 |
| Caffeine | 3.78 | 4.10 |
| | 100.00 | 100.00 |

[1] Flavor added in 2 additions after 10th and 15th within coating syrup 1.

Initial center piece weight was 0.956 grams. Gum was coated to a finished piece weight of 1.46 grams to give a 34.5% coating. Coating syrup 1 was used to coat the first 60% of the coating to a piece weight of 1.26 grams. Coating syrup 2 was used to coat to the final piece weight. Individual piece analysis of 5 pieces yielded a level of 26.1 mg of caffeine per piece. For a 2 piece dosage, caffeine level is 52.2 mg.

This gum product was used in a caffeine absorption study to compare release and absorption uptake of caffeine from gum and beverages. The test results showed that gum is a faster delivery vehicle for caffeine when compared to the same level in beverages as measured by blood plasma caffeine. Caffeine was taken up faster in the test subject's plasma after delivery via gum than after delivery of same caffeine dose via coffee, cola, and tea.

Comparisons of caffeine delivery between chewing gum and the three beverages are demonstrated by statistically significant differences in one or more of the following parameters:
1. Plasma caffeine concentration is significantly greater for gum vs. beverages within the first 10 to 30 minutes after caffeine delivery. This correlates to faster uptake.
2. Plasma absorption rate constant (A-rate) larger for gum vs. one or more beverages (2). Plasma absorption half life (abs. half-life) smaller for gum vs. one or more beverages (2). Time of peak caffeine plasma. A clinical trial study was performed where six subjects participated in the test, blood was drawn and plasma separated. Blood sampling occurred prior to, and at present time intervals following a caffeine level of 50–55 mg released through the test delivery vehicle. Five different studies were completed: gum (with saliva swallowed, G2), gum (with saliva expectorated, G3), coffee (ingested COF), cola (ingested COK), and tea (ingested T). Blood samples of 5 ml were collected and the plasma portion separated, stored, and extracted and analyzed. A method was developed for the extraction and analysis of caffeine in fluids, which reports results as the concentration of caffeine in the plasma.

Data from the six subjects participating in the study were compiled, analyzed, and graphed, with mean plasma caffeine concentrations at specific time intervals determined. Analysis of variance (ANOVA) were performed on the means to determine statistical significance.

Phamacokinetic parameters were determined through Wagner's 1967 Method of Residuals using a pharmacokinetic software package. Absorption rate constants and absorption half-life were also determined through the analysis of the absorption phase of the plots by linear regression since the absorption phase followed zero order kinetics.

The conclusions were as follows:

1. There was a faster uptake of caffeine in plasma during the early time intervals post dose 10 minutes to 25 minutes (T10–T25) via gum delivery vs. the same level of caffeine delivered via coffee and cola. For example, the average level of plasma caffeine (at T=10 minutes) present after gum chew is 0.545 µg/ml compared to 0.186 µg/ml for coffee and 0.236 µg/ml for cola. In other words, with the same level of caffeine being delivered from the three different vehicles, at T10 there is 3 times more caffeine present in plasma after chewing gum than from ingesting coffee and 2 times more caffeine from gum than from cola. The results of the tea study proved to be too variable due to instrument problems and repeat freeze/thawing of the samples. They were not included in the calculations.

2. Classical pharmacokinetic parameters, T-max, A-rate constant, abs. half-life, do not tell the story of faster uptake in the time interval of interest (T10–T25) in this study. This is due in part to the calculation using the Method of Residuals. This method was derived using classical pharmacokinetic curves which do not have much fluctuation in the data in that the drug concentration (usually measured every hour) increases to a sharp T-max, then decreases, without any fluctuation. In comparison, the data did contain minor fluctuations, due most likely to a combination of factors: measurement of plasma concentrations every five minutes rather than every quarter hour to one hours, caffeine binding with plasma protein, combination of both sublingual and gut absorption being detected. The plasma caffeine concentration followed the same trends as in classical pharmacokinetic curves, except that the concentration increased to a broad T-max, then decreased, and some of the points in the curve fluctuated up and down.

A-rate constant and abs. half-life determinations were also made through linear regression. No significant differences were noted in the means, though a trend was noted: the A-rate for the gum study (G2) was greater than that for coffee and cola for subjects 1–4 and the abs. half-life for the G2 study was less than that for coffee and cola for subjects 1–4. For example, the G2 abs. half-life averaged 13±4 minutes for subjects 1–4, 28±2 minutes for subjects 5 and 6, indicating faster absorption between the subjects. The amount of caffeine absorbed sublingually was 21±7 mg for subjects 1–4, and 10±1 mg for subjects 5 and 6 accounting for the increased A-rate and decreased abs. half-life in subjects 1–4. An ANOVA separating subjects 1–4 from 5 and 6 indicated that for subjects 1–4 cola abs. half-life is statistically greater than G2 abs. half-life (p=0.10), and the G2 A-rate is statistically greater than both the cola and coffee A-rate (p=0.05).

3. It was shown that significant levels of caffeine are absorbed sublingually directly into the bloodstream via delivery from gum. This was demonstrated through the testing of caffeinated gum where the saliva was expectorated. Even though the saliva was expectorated, 20–50% of the caffeine was absorbed through the oral cavity. This accounts for the early uptake into the bloodstream.

Experiment No. 2

The following formulation was made:

| Gum Center | % |
|---|---|
| Gum Base | 33.00 |
| Calcium Carbonate | 13.00 |
| Sorbitol | 44.23 |
| Glycerin | 4.00 |
| Flavors | 2.32 |
| Encapsulated Caffeine[2] | 1.50 |
| Free Caffeine | 0.45 |
| Lecithin | 0.60 |
| Encapsulated Sweeteners | 0.90 |
| | 100.00 |

| Gum Coating | Coating Syrup 3.0% | Coating Syrup 4.0% |
|---|---|---|
| Xylitol | 64.14 | 76.23 |
| Water | 11.14 | 13.15 |
| 40% Gum Tahla Solution | 20.87 | 7.96 |
| Titanium Dioxide Whitener | 0.40 | 0.40 |
| Peppermint Flavor[3] | 1.40 | 0.00 |
| Sweeteners | 0.27 | 0.27 |
| Carnauba Wax/ | 0.00 | 0.27[4] |
| Talc Polishing Agents | | |
| Caffeine | 1.78 | 1.72 |
| | 100.00 | 100.00 |

[2]Spray dried maltodextrin/caffeine at 50% active caffeine.
[3]Flavor added in 3 additions after 3 separate syrup addition within coating syrup 1.
[4]Polished after completion of coating.

Initial center piece weight was 0.995 grams. Gum was coated to a finished piece weight of 1.52 grams to give a 34.5% coating. Coating syrup 3 was used to coat the first 60% of the coating to a piece weight of 1.30 grams. Coating syrup 4 was used to coat to the final piece weight. Individual piece analysis of 5 pieces yielded a level of 20.0±0.8 mg of caffeine per piece. For a two piece dosage, caffeine level is 40.0 mg.

This gum product was used in a caffeine absorption study to compare release and absorption uptake of caffeine from gum versus pills. The test results showed that gum is a faster delivery vehicle for caffeine when compared to a similar level in a pill as measured by blood plasma caffeine. Caffeine was taken up faster in the test subject's plasma after delivery via gum than after delivery of same caffeine dose via a pill.

Data from the six subjects participating in each study were compiled, analyzed, and graphed, with mean plasma caffeine concentrations at specific time intervals determined. Analysis of variance (ANOVA) and Student t-Tests were performed on the means to determine statistical significance. Pharmacokinetic parameters were done using a pharmacokinetic software package. The gums tested were pellet from Experiment No. 5, containing all the caffeine in the coating and delivering approximately 50 mg caffeine after chewing two pellets (designated as G2, G4, or 50 mg pellet), and Experiment No. 6, containing caffeine in the coating and center, and delivering approximately 40 mg caffeine after chewing two pellets (designated G5 or 40 mg pellet). Both pellets were compared to Pro-Plus™ 50 mg tablet is manufactured by the product license holder: PP Products, 40 Broadwater Road, Welayn Garden City, Harts, AL7 Bay, UK. Caffeine analysis were analyzed at 48.3 mg ±1.4 mg caffeine per pill (avg. of n=5).

It was concluded that caffeine uptake in the bloodstream was faster for gum than a pill, based on the following:

1. Faster uptake of plasma caffeine via gum delivery was found during the early time intervals post dose 5 minutes to 50 minutes (T5–T50) when compared to the same level of caffeine delivered via a pill (50 mg). For example, with the same level of caffeine being delivered from the two different vehicles, on average, at T5 there is 30 times more caffeine detected in plasma after chewing gum (0.205 μg/ml). Average plasma caffeine levels significantly greater than the pill at a=0.01 for T5, and a=0.005 for T10.

2. Classical pharmacokinetic parameters, T-Max (time for peak plasma caffeine concentration) and Abs. half-life (absorbence half-life, time for caffeine concentration to be half of peak) were significantly different for caffeine delivered via 50 mg pellet gum (Experiment No. 5) than via a 50 mg pill. Faster uptake of plasma caffeine was demonstrated via delivery from gum compared to a pill due to the average plasma Abs. half-life and average plasma T-Max being significantly smaller for gum than the pill. For the 50 mg pellet gum, the average Abs. half-life=12.84 min. and the average T-Max=36.5 min. compared to the 50 mg pill with an average Abs. half-life=24.47 min (pill significantly greater than gum, a=0.0075), and an average T-Max=73.67 min (pill significantly greater than gum, a=0.0075), and an average T-Max=73.67 min (pill significantly greater than gum, a=0.005). In other words, after ingesting a pill, it takes a longer amount of time to reach half of the peak plasma caffeine concentration and the peak plasma caffeine concentration than after chewing gum delivering the same level of caffeine.

3. The Abs. Rate Const. (absorption rate constant, rate at which caffeine absorbs into the bloodstream) was significantly greater for 50 mg pellet gum (Experiment No. 5) than for the 50 mg pill, indicating that caffeine is absorbed at a greater rate after gum delivery than after delivery of the same dosage via a pill. For the 50 mg pellet gum, the average Abs. Rate Const.=0.060 compared to the 50 mg pill with an average Abs. Rate const.=0.031 (gum significantly greater than pill, a=0.005).

4. The test also demonstrated faster uptake of plasma caffeine via the product of Experiment No. 6, 40 mg pellet gum, delivery during the early time intervals post dose 10 minutes to 30 minutes (T10–T30) when compared to 50 mg of caffeine delivered via a pill. Significance levels ranged from a=0.05 to a=0.20. For example, the average level of plasma caffeine (at T=10 minutes) present after 40 mg pellet gum is chewed is 0.228 μg/ml compared to 0.034 μg/ml for pill (difference was slightly significant, a=0.2). In other words, with caffeine being delivered from the two different vehicles at T10 there is 6.7 times more caffeine detected in plasma after chewing the product of Experiment No. 6 gum caffeine than after ingesting a pill, even though the pill delivered approximately 50 mg caffeine, and the product of Experiment No. 6 delivered approximately 40 mg. At T5, on average there was 13 times more caffeine detected in plasma after chewing Experiment No. 6 gum than after ingesting a pill.

5. Classical pharmacokinetic parameters, T-Max and Abs. half-life were significantly different for caffeine delivered via the product of Experiment No. 640 mg pellet gum than via a 50 mg pill. Faster uptake of plasma caffeine was demonstrated via delivery from the product of Experiment No. 6 gum compared to a pill due to the average plasma Abs. half-life and average plasma T-Max being significantly smaller for gum than the pill. For the 50 mg Experiment No. 5 gum, the average Abs. half-life=18.33 min. and the average T-Max=45 min compared to the 50 mg pill with an average Abs. half-life=24.47 min (pill significantly greater than pill, a=0.05), and an average T-Max=73.67 min (pill significantly greater than gum, a=0.15). Even though the product of Experiment No. 6 delivered 40 mg caffeine compared to delivery of 50 mg via a pill, it still took a longer amount of time to reach half of the peak plasma caffeine concentration for the pill than for the gum.

6. It was concluded that gums formulated with all the caffeine in the pellet coating delivered caffeine more quickly to the plasma than gums formulated with the caffeine split between the coating and the center based upon the following:

Classical pharmacokinetic parameters T-Max and Abs. half-life were greater than pill for both 50 mg pellet and Experiment No. 5 though the level of significant different was much greater for the 50 mg pellet (Experiment No. 5) (a=0.0075 and a=0.005 respectively) than the product of Experiment No. 6 (a=0.05, a=0.15). The Abs. Rate Const. was significantly lower for the pill than for either the 50 mg pellet or the the product of Experiment No. 6. Again, the level of significant difference was greater for the 50 mg pellet (Experiment No. 5), a=0.005 compared to 0.20 for the product of Experiment No. 6.

7. Combining the conclusions from the two completed caffeine studies, it appears that rate of caffeine uptake in plasma via the various delivery vehicles tested follow this pattern:

Pellet with caffeine all in coating>Pellet with caffeine split between coating and center=Beverages coffee/cola>Pill Caffeine was chosen as a model for drug delivery tests because it is a food approved, pharmacologically active agent that is readily detected in plasma at a wide range of dosage levels. It is widely consumed via a number of delivery vehicles, including liquids (coffee, cola, and pills). Drugs are administered through different delivery vehicles, two oral delivery vehicles being liquid syrups and pills. Testing caffeinated beverages and pills vs. caffeinated gums should give an indication of how similar drugs administered as liquids or coated pills vs. coated gums could behave.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

We claim:

1. A method for delivering a medicament to an individual comprising the steps of:
   providing a product that comprises tableted center and a coating that substantially surrounds the tableted center, the tableted center being defined by at least one compressible excipient, the coating containing a medicament and comprising at least 50% by weight of the product; and
   chewing the product to cause the medicament to be released from the product into the buccal cavity of the individual.

2. The method of claim 1 wherein the coating comprises a high-intensity sweetener.

3. The method of claim 1 wherein the high-intensity sweetener is selected from the group consisting of aspartame, sucralose, saccharin, and acesulfame-k.

4. The method of claim 1 wherein the coating is produced by alternating layers of a powder and a syrup onto the tableted center.

5. The method of claim 1 wherein the tableted center comprises at least one excipient selected from the group consisting of compressible sacharides and compressible sugar alcohols.

6. The method of claim 1 wherein the medicament is selected from the group consisting of: analgesics; muscle relaxants; antibiotics; antivirals; antihistamines; decongestants; anti-inflammatories; antacids; psychotherapeutic agents; insulin; vitamins; minerals; nutraceuticals; nutritional supplements; and cardiovascular agents.

7. The method of claim 1 wherein the coating has a polished finish.

8. A method of delivering a medicament comprising the steps of:

providing a product having a tableted center and a coating that substantially surrounds the center, the center comprising at least one compressible excipient and the coating comprising a medicament and comprising at least 50% by weight of the product; and chewing the product to release the medicament into a buccal cavity of an individual chewing the product.

9. The method of claim 8 wherein the medicament is selected from the group consisting of: analgesics; muscle relaxants; antibiotics; antivirals; antihistamines; decongestants; anti-inflammatories; antacids; psychotherapeutic agents; nutraceuticals; nutritional supplements; and cardiovascular agents.

10. The method of claim 8 wherein the tableted center includes a saccharide or sugar alcohol.

11. A method for delivering a medicament to an individual comprising the steps of:

providing a product that comprises a center that has a precise shape and a coating that substantially surrounds the center, the center being defined by at least one compressible excipient, the coating containing a medicament and comprising at least 50% by weight of the product; and chewing the product to cause the medicament to be released from the product into the buccal cavity of the individual.

12. The method of claim 11 wherein the center comprises at least one excipient selected from the group consisting of compressible sacharides and compressible sugar alcohols.

13. The method of claim 11 wherein the medicament is selected from the group consisting of: analgesics; muscle relaxants; antibiotics; antivirals; antihistamines; decongestants; anti-inflammatories; antacids; psychotherapeutic agents; insulin; vitamins; minerals; nutraceuticals; nutritional supplements; and cardiovascular agents.

14. A method of delivering a medicament comprising the steps of:

providing a product having a uniform center and a coating that substantially surrounds the center, the center comprising at least one compressible excipient and the coating comprising a medicament and comprising at least 50% by weight of the product; and chewing the product to release the medicament into a buccal cavity of an individual chewing the product.

15. The method of claim 14 wherein the medicament is selected from the group consisting of: analgesics; muscle relaxants; antibiotics; antivirals; antihistamines; decongestants; anti-inflammatories; antacids; psychotherapeutic agents; nutraceuticals; nutritional supplements; and cardiovascular agents.

* * * * *